United States Patent
Zhou et al.

(10) Patent No.: US 7,027,856 B2
(45) Date of Patent: Apr. 11, 2006

(54) METHOD FOR DETERMINING A METRIC OF NON-SUSTAINED ARRHYTHMIA OCCURRENCE FOR USE IN ARRHYTHMIA PREDICTION AND AUTOMATIC ADJUSTMENT OF ARRHYTHMIA DETECTION PARAMETERS

(75) Inventors: Xiaohong Zhou, Plymouth, MN (US); Bruce D. Gunderson, Plymouth, MN (US); Walter H. Olson, North Oaks, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 10/261,316

(22) Filed: Sep. 30, 2002

(65) Prior Publication Data

US 2004/0064062 A1    Apr. 1, 2004

(51) Int. Cl.
*A61B 5/0452*    (2006.01)
(52) U.S. Cl. .................................... 600/515
(58) Field of Classification Search ......... 600/515–518
See application file for complete search history.

(56) References Cited

U.S. PATENT DOCUMENTS

| | | | |
|---|---|---|---|
| 4,458,691 A | | 7/1984 | Netravali |
| 4,830,006 A * | | 5/1989 | Haluska et al. ................ 607/4 |
| 5,042,497 A | | 8/1991 | Shapland |
| 5,117,824 A | | 6/1992 | Keimel et al. |
| 5,271,393 A | | 12/1993 | Callaghan |
| 5,277,190 A * | | 1/1994 | Moulton ..................... 600/518 |
| 5,318,592 A | | 6/1994 | Schaldach |
| 5,545,186 A | | 8/1996 | Olson et al. |
| 5,658,318 A | | 8/1997 | Stroetmann et al. |
| 6,067,473 A | | 5/2000 | Greeninger et al. |
| 6,115,627 A | | 9/2000 | Street |
| 6,134,470 A | | 10/2000 | Hartlaub |
| 6,272,377 B1 | | 8/2001 | Sweeney et al. |
| 6,308,094 B1 | | 10/2001 | Shusterman et al. |
| 6,718,198 B1 * | | 4/2004 | Conley et al. ................ 60/523 |

OTHER PUBLICATIONS

"Arrhythmias after acute myocardial infarction," Postgraduate Moedicine, vol. 102, No. 5 (Nov. 1997).*
Schmidt et al., "Heart Rate Turbulence After Ventricular Premature Beats as a Predictor of Mortality After Acute Myocardial Infarction," *Lancet*, vol. 353, p. 1390-6 (1999).
Shusterman et al., "Autonomic Nervous System Activity and the Spontaneous Initiation of Ventricular Tachycardia," *J Am Coll Cardiol*, vol. 32, p. 1891-9 (1998).

* cited by examiner

*Primary Examiner*—George Manuel
*Assistant Examiner*—Nicole R. Kramer
(74) *Attorney, Agent, or Firm*—Michael C. Soldner; Girma Wolde-Michael

(57) ABSTRACT

An implantable medical device and associated method are provided for detecting non-sustained arrhythmias and determining a metric of non-sustained arrhythmias. The metric may be used for predicting the occurrence of a sustained arrhythmia or for automatically adjusting the parameters used for detecting a sustained arrhythmia.

6 Claims, 9 Drawing Sheets

METHOD FOR DETERMINING A METRIC OF NON-SUSTAINED ARRHYTHMIA OCCURRENCE FOR USE IN ARRHYTHMIA PREDICTION AND AUTOMATIC ADJUSTMENT OF ARRHYTHMIA DETECTION PARAMETERS

FIELD OF THE INVENTION

The present invention relates to medical devices for detecting, predicting and treating arrhythmias and, more specifically, to a method for determining a metric of non-sustained cardiac arrhythmias for use in predicting the occurrence of sustained cardiac arrhythmias or automatically adjusting arrhythmia detection parameters.

BACKGROUND OF THE INVENTION

Ventricular tachycardia (VT) and ventricular fibrillation (VF) are serious, life-threatening forms of cardiac arrhythmias. Implantable cardioverter defibrillators, or "ICDs", are capable of automatically detecting arrhythmias and delivering anti-arrhythmia therapies. Delivering anti-tachycardia pacing therapies or high-energy shock therapies may terminate VT and VF. Ventricular tachycardia termination is typically referred to as "cardioversion." Ventricular fibrillation termination is typically referred to as "defibrillation."

Detection of an arrhythmia by an ICD is generally determined by comparing the sensed heart rate to predetermined, programmable parameters. The intervals between sensed events in the atria, referred to P-waves, and/or sensed events in the ventricles, referred to as R-waves, may be used to determine a heart rate. Generally, the interval between two sensed cardiac events, an R—R interval in the ventricle or a P—P interval in the atrium, is compared to a set of programmable detection intervals. For example a sensed R—R interval may be compared to a specified VT detection interval, a fast VT detection interval and a VF detection interval. If the sensed R—R interval is less then any one of these intervals, it is classified as such. Arrhythmia detection is made when a specified number of intervals in a detection interval range is reached. For example, a nominal setting for detecting VT may be 16 consecutively sensed intervals less than 400 ms. A nominal setting to detect VF may be 18 of the last 24 sensed intervals must be less than 320 ms. These settings may be adjusted according to patient need, however, once programmed by a clinician, generally remain fixed until the next programming session.

Nearly all of detected arrhythmias appropriately treated by an ICD do not result in death. However, ICD therapies can be very painful to the patient, and compromised hemodynamic output during a VT or VF episode can render a patient unconscious resulting in related serious injuries or death. Because of the serious consequences of cardiac arrhythmias, it is desirable to predict the occurrence of an arrhythmia so that preventive measures may be taken to avert the arrhythmia entirely.

Arrhythmia prevention therapies can include medical regimes, pacing regimes, or involve neurostimulation such as spinal cord stimulation. Reference is made to U.S. Pat. No. 6,134,470 issued to Hartlaub, incorporated herein by reference in its entirety. Continuous delivery of arrhythmia prevention therapies may not be practical due to side effects, cost or other factors. Reliable prediction of an imminent arrhythmia would allow preventative therapies to be delivered only when needed. An arrhythmia prediction must be made in ample enough time to allow a preventative therapy to be effective. The prediction time required will depend on the type of therapy to be delivered and may vary from on the order of a day, several hours, several minutes or several seconds.

A number of parameters for predicting a discrete VT or VF episode have been proposed including, for example, left ventricular dysfunction, myocardial ischemia, frequency of ventricular ectopic beats, heart rate variability, heart rate turbulence, or other electrocardiographic changes (see Shusterman et al., J Am Coll Cardiol. 1998;32:1891–9, and Schmidt et al., Lancet. 1999;353:1390–96). Changes in the autonomic nervous system are known contributing factors to arrhythmogenesis. The heart rate is normally regulated by a balance between the sympathetic and parasympathetic (vagal) components of the autonomic nervous system. Increased sympathetic activity, referred to as sympathetic tone, increases the heart rate and decreases heart rate variability. Increased vagal tone decreases the heart rate and increases heart rate variability. Heart rate variability (HRV) is the variation in consecutive heart rate cycles. Changes in autonomic tone, especially in conjunction with myocardial ischemia can play an important role in the development of arrhythmias. Therefore, indicators of changes in autonomic tone may be useful in predicting arrhythmias. Reference is made to U.S. Pat. No. 5,042,497 issued to Shapland, U.S. Pat. No. 5,318,592 issued to Schaldach, and U.S. Pat. No. 5,658,318 issued to Stroetmann et al.

Other methods for predicting arrhythmias based on changes in a sensed cardiac electrograms (EGM) or a patient's ECG are generally disclosed in U.S. Pat. No. 6,115,627 issued to Street, U.S. Pat. No. 6,308,094 issued to Shusterman, U.S. Pat. No. 4,458,691 issued to Netravali, and U.S. Pat. No. 5,271,393 issued to Callaghan. In U.S. Pat. No. 6,272,377 issued to Sweeney et al., an estimated arrhythmia probability is calculated based on detected conditioning events statistically associated with an arrhythmia.

Patients may also experience non-sustained arrhythmias, which terminate spontaneously without any medical intervention. Arrhythmia detection algorithms used by ICDs typically discriminate between a non-sustained arrhythmia and a sustained arrhythmia based only on static detection parameters regarding the duration of the arrhythmia. Arrhythmia detection is generally absolute in that either a detection is made, followed by an associated treatment, or no detection is made and no treatment is delivered. The difference between a sustained arrhythmia requiring treatment and a non-sustained arrhythmia that spontaneously terminates is generally determined by fixed arrhythmia detection parameters programmed by a physician. For example, if the number of intervals required to detect an arrhythmia is programmed to 16, an arrhythmia that lasts 15 intervals long and spontaneously terminates will not be detected at all, while an arrhythmia that lasts at least one interval longer will be detected and may be treated.

The inventors of the present invention hypothesize that the underlying factors that may trigger a sustained arrhythmia may be the same factors that trigger a non-sustained arrhythmia. A sustained arrhythmia may represent a worsening condition of these factors, which, in a less severe state, trigger arrhythmias that spontaneously terminate. A worsening condition, it is hypothesized, may first present itself as an increase in the frequency or duration of non-sustained arrhythmias and ultimately in a sustained arrhythmia. Other changes in the characteristics of non-sustained arrhythmias, such as EGM changes related to the cycle length and signal morphology, may move toward that typical during a sustained arrhythmia.

In a retrospective study of ICD patients performed by the inventors, patients having episodes of non-sustained VT were much more likely to experience a sustained VT or VF episode than patients that did not experience non-sustained VT episodes. Furthermore, the number of non-sustained episodes and the total number of non-sustained arrhythmia cycles per day increased dramatically on the day that a sustained VT or VF occurred. The atrial interval (PP interval) and ventricular interval (RR interval) during non-sustained VT became more similar to the PP and RR intervals measured during a sustained VT. Thus, the inventors of the present invention hypothesize that trends in the incidence of non-sustained arrhythmias may be useful predictors of the occurrence of a sustained arrhythmia. It is desirable therefore, to provide a method for monitoring the incidence of non-sustained arrhythmias and for determining a metric of non-sustained arrhythmias within an individual patient. Such a metric may be used for predicting the occurrence of a sustained arrhythmia.

Such a metric may also be useful in adjusting arrhythmia detection parameters to improve the ability of the ICD to dynamically discriminate between non-sustained and sustained arrhythmia episodes. Patients that experience frequent non-sustained arrhythmia episodes may be exposed to repeated anti-arrhythmia therapies if recurring non-sustained arrhythmias are detected by the ICD according to static detection parameters, before the episode has time to self-terminate. Anti-arrhythmia therapies can be painful to the patient, consume ICD battery energy, and, in some cases, accelerate or otherwise worsen the severity of the arrhythmia.

By dynamically adjusting arrhythmia detection parameters based on a metric of non-sustained arrhythmias, the delivery of unneeded anti-arrhythmia therapies may be reduced, conserving battery energy needed for terminating sustained arrhythmias and sparing the patient potentially painful therapies. Moreover, the metric of non-sustained arrhythmias may be used for the successful prediction of a sustained arrhythmia that would allow arrhythmia prevention therapies to successfully avert the need for anti-arrhythmia therapies, prevent other injuries that can occur with an arrhythmia, and, most importantly, prevent potentially fatal arrhythmias from occurring.

SUMMARY OF THE INVENTION

The present invention addresses the above described needs by providing a method for determining a metric of non-sustained arrhythmias. This metric may be used to predict the occurrence of a sustained arrhythmia and thereby allow an arrhythmia prevention therapy to be delivered. This metric of non-sustained arrhythmias may also be used to adjust parameters used in detecting a sustained arrhythmia.

The present invention is realized in an implantable medical device (IMD) capable of sensing cardiac signals, detecting non-sustained cardiac arrhythmia episodes and determining a metric of non-sustained arrhythmia episodes. The IMD may also be capable of providing cardioversion and defibrillation therapy and/or arrhythmia prevention therapies. The IMD is preferably equipped with a data acquisition system for collecting data related to non-sustained arrhythmias and a memory for storing data. A central processing unit for controlling device functions, such as the detection and treatment of cardiac arrhythmias, is also used for processing data in order to determine a number of variables used for calculating a metric of non-sustained arrhythmias.

Variables of interest include, but are not limited to, the number of non-sustained arrhythmias occurring during a specified period of time, the duration of the non-sustained arrhythmias, the atrial and/or ventricular intervals during the non-sustained arrhythmias, and characteristics of the EGM morphology during non-sustained arrhythmias. One or more of these variables may be used to determine one or more non-sustained arrhythmia metrics. The metric(s) may then be used in other device operations, for example, for predicting the occurrence of a sustained arrhythmia or automatically adjusting arrhythmia detection parameters.

In operation, non-sustained arrhythmia episodes are detected according to non-sustained arrhythmia detection criteria and the related variables of interest are stored in memory. A non-sustained arrhythmia metric may be updated upon each non-sustained arrhythmia detection or following a specified period of time. In a method for predicting a sustained arrhythmia, an arrhythmia risk score is calculated based on one or more non-sustained arrhythmia metrics. Each time a risk score is calculated, it is compared to a predetermined arrhythmia prediction threshold. If the risk score crosses the prediction threshold, a sustained arrhythmia is predicted to occur with a high probability. Prediction of a sustained arrhythmia may trigger the delivery of an arrhythmia prevention therapy, which can include pacing therapies, drug therapies, or neurostimulation. A patient may be alerted to a predicted arrhythmia by an audible sound or other notification method so that the patient may alter their current activity or seek medical attention.

A non-sustained arrhythmia metric may alternatively or additionally be used for automatically adjusting one or more sustained arrhythmia detection parameters. In a preferred embodiment, the number of intervals required to detect a sustained arrhythmia is automatically adjusted based on the duration of detected non-sustained episodes. If a trend of increasing duration of non-sustained arrhythmias is occurring, therapy delivery during an arrhythmia that is likely to self-terminate is avoided by increasing the number of intervals required to detect a sustained arrhythmia.

The present invention thus provides a method for monitoring the occurrence of non-sustained arrhythmias and determining an associated metric of non-sustained arrhythmias. The present invention further provides a method for predicting the occurrence of a sustained arrhythmia based on the occurrence of non-sustained arrhythmias in a particular patient, which may indicate a worsening condition of the substrate associated with triggering a sustained arrhythmia. The methods included in the present invention allow arrhythmia prediction criteria to be tailored to an individual patient. Furthermore, methods included in the present invention allow adjustments to be made to sustained arrhythmia detection parameters based on episodes of non-sustained arrhythmia, potentially reducing the number of anti-arrhythmia therapies that may be delivered during episodes that could self-terminate.

DETAILED DESCRIPTION OF THE INVENTION

As described above, the present invention is aimed at determining a metric of non-sustained arrhythmias. The methods included in the present invention may be incorporated in an implantable or external monitoring device, or an implantable or external cardiac rhythm management device. In a preferred embodiment, the methods of the present invention are incorporated in an implantable cardiac device capable of monitoring the heart rhythm for detecting arrhythmias and delivering anti-arrhythmia therapies, such as the implantable cardioverter defibrillator (ICD) 10 shown in FIG. 1.

Figure 1:
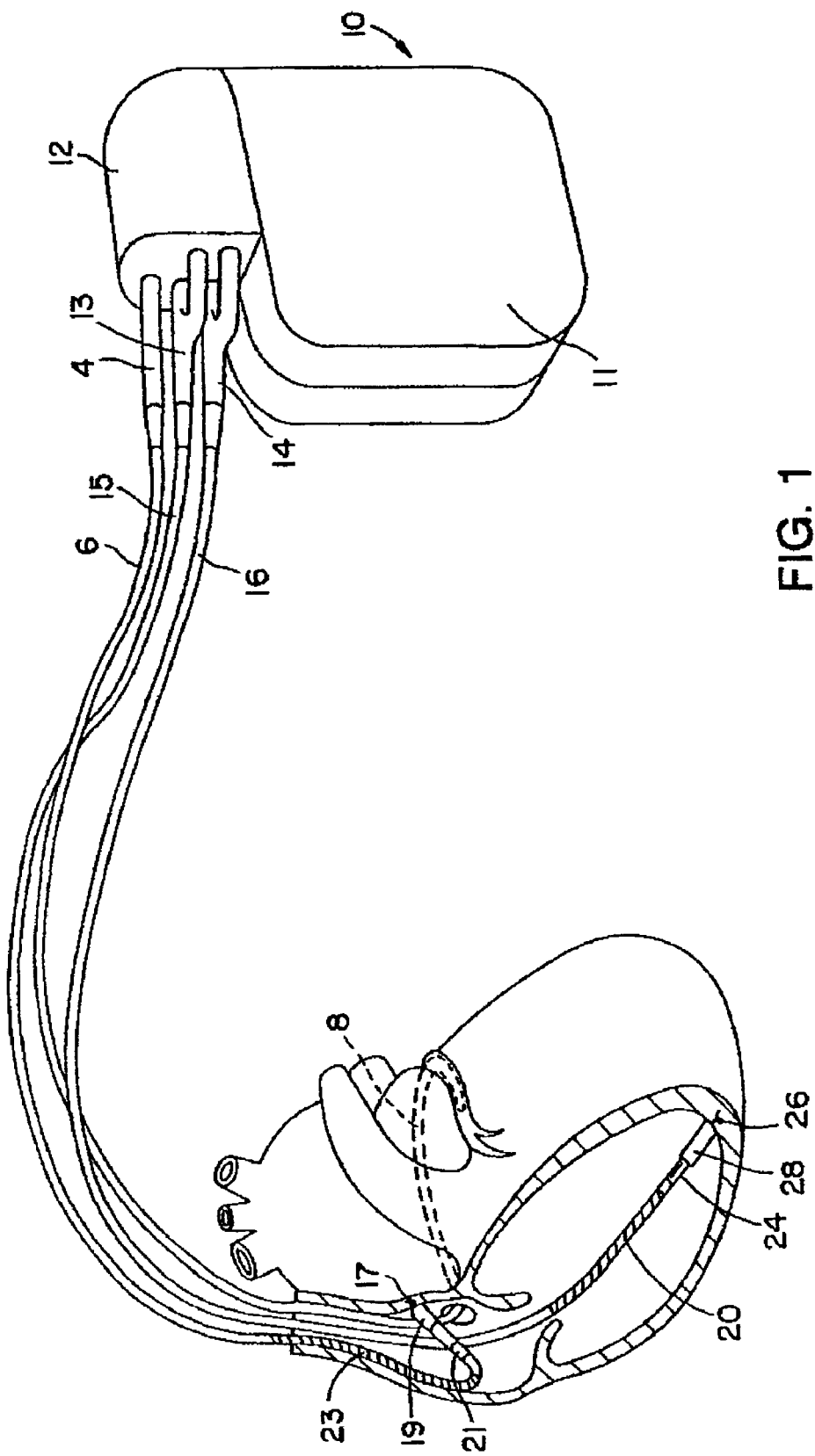
FIG. 1 is an illustration of an exemplary implantable cardiac stimulation device, capable of pacemaking, cardioversion, and defibrillation, in communication with a patient's heart via three stimulation and sensing leads.

The exemplary ICD 10 is shown coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the coil electrodes 8, 20 or 23 for defibrillation of the atria or ventricles. It is recognized that alternate lead systems may be substituted for the three lead system illustrated in FIG. 1.

Although three or four-chamber pacing, cardioversion and defibrillation capacity is not necessary for practicing the invention, and indeed detection of an arrhythmia can be determined by sensing only signals derived from one heart chamber, a multi-chamber system is illustrated so as to indicate the scope of the invention. It is understood that the invention may normally be practiced with a multi-chamber, dual chamber, or single chamber device connected to an associated lead system including at least a sensing electrode pair for sensing cardiac signals.

Figure 2:
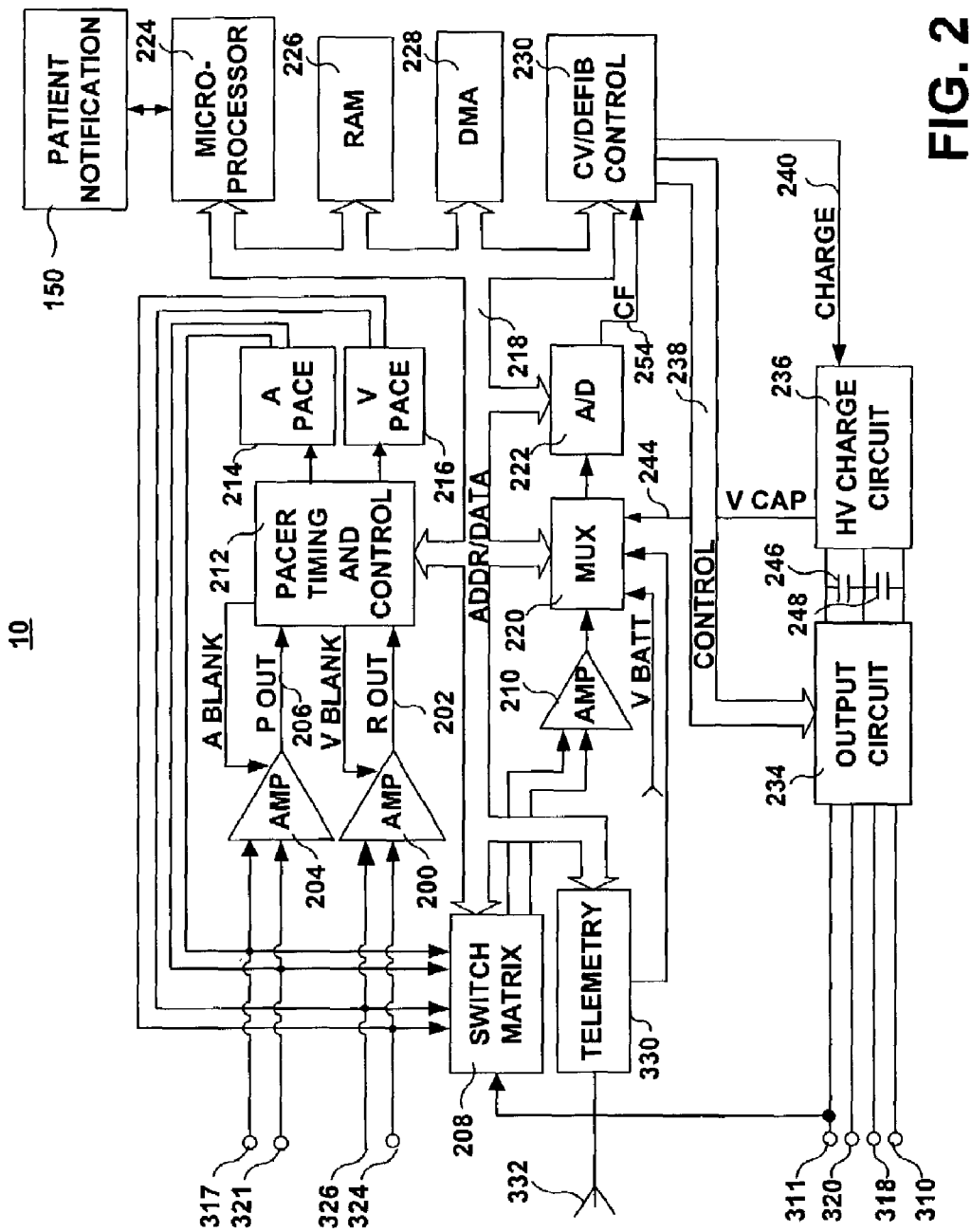
FIG. 2 is a functional, block diagram of the implantable cardiac stimulation device shown in FIG. 1.

A functional schematic diagram of the ICD 10 is shown in FIG. 2. This diagram should be taken as exemplary of the type of device in which the invention may be embodied and not as limiting. The disclosed embodiment shown in FIG. 2 is a microprocessor-controlled device, but the methods of the present invention may also be practiced in other types of devices such as those employing dedicated digital circuitry.

With regard to the electrode system illustrated in FIG. 1, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 28 respectively. Each of these connection terminals 311, 320, 310, and 318 are coupled to the high voltage output circuit 234 to facilitate the delivery of high energy shocking pulses to the heart using one or more of the coil electrodes 8, 20, and 28 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals such as R-waves.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. A tachyarrhythmia recognition mechanism is described in the previously referenced U.S. Pat. No. 5,545,186 issued to Olson et al, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used. The telemetry circuit 330 is also used for communication with a patient activator in one embodiment of the present invention.

The device 10 may be equipped with a physiological sensor 344 and sensor processing circuitry 342. Depending on the type of sensor used, the sensor 344 may be located within the device housing 10 or external to the device housing 10 but implanted within the body of the patient. In one embodiment, the sensor 344 may take the form of a piezoelectric crystal used for determining the patient's activity level.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer, circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R—R intervals and P—P intervals for detecting the occurrence of a variety of arrhythmias.

The microprocessor 224 includes associated ROM in which stored programs controlling the operation of the microprocessor 224 reside. A portion of the memory 226 may be configured as a number of re-circulating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 220 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150 used to notify the patient that an imminent, sustained arrhythmia episode is predicted. Any known patient notification method may be used such as generating a perceivable twitch stimulation or an audible sound under the control of microprocessor 224. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
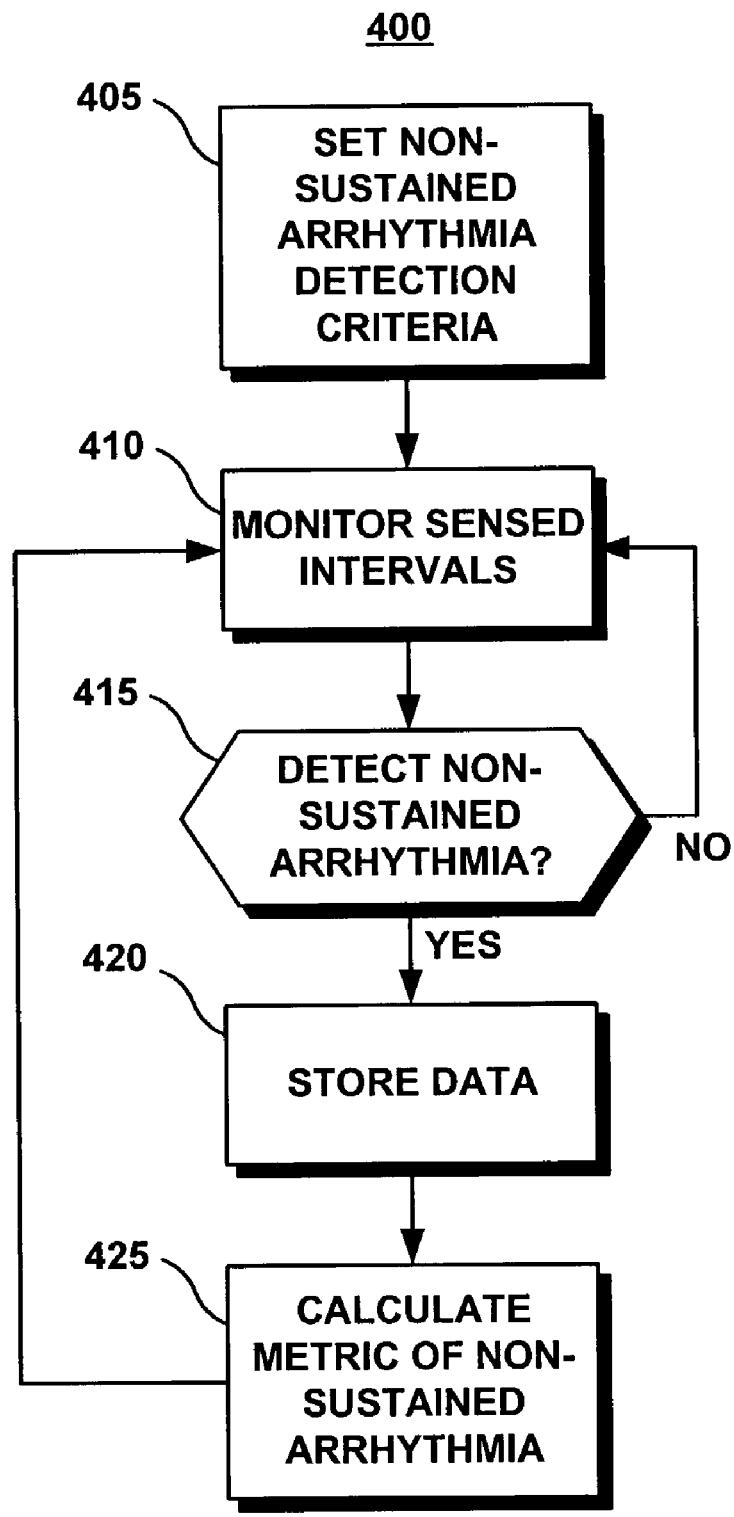
FIG. 3 is a flow diagram providing an overview of operations included in the present invention for determining a metric of non-sustained arrhythmias.

FIG. 3 is a flow diagram providing an overview of operations included in the present invention for determining a metric of non-sustained arrhythmia. The steps illustrated in FIG. 3 are preferably carried out under the control of microprocessor 224. The method 400 begins at step 405 by setting criteria for detecting a non-sustained arrhythmia. A non-sustained arrhythmia episode may be discriminated from a sustained episode by defining a unique set of detection parameters for each. Detection parameters defining the maximum interval length and the required number of intervals to detect a non-sustained arrhythmia may be defined at step 405. The maximum interval length may be the same interval used for detecting a sustained arrhythmia. The number of intervals required for detecting a non-sustained arrhythmia may be any number less than the number of intervals required for detecting a sustained arrhythmia. A number greater than 1 is preferred since one short sensed interval may be associated with a premature contraction or various causes of oversensing. An example of non-sustained VT detection criteria may be at least 3, preferably at least 5, intervals less than 400 ms, while sustained VT detection criteria may be at least 16 intervals of less than 400 ms.

At step 410, pacer timing and control 212 monitors the sensed intervals as indicated by signals on P-out line 206 and/or R-out line 202. If microprocessor 224 determines, based on the sensed intervals and according the criteria set at step 405, that a non-sustained arrhythmia is detected at decision step 415, data regarding the non-sustained arrhythmia episode is collected and stored in memory 226 at step 420. After collecting data from a desired number on non-sustained episodes or from all non-sustained episodes occurring in a predetermined period of time, a metric of non-sustained arrhythmias is calculated at step 425. The metric is stored in memory 226 and may be used by microprocessor 224 in other processes, such as algorithms for predicting a sustained arrhythmia or algorithms for automatically adjusting sustained arrhythmia detection parameters as will be described herein. The metric may also be stored in a log that may be downloaded for review by a physician. Such information may be useful to a physician in monitoring a patient's disease state or selecting treatment options. The method 400 may then be repeated by returning to step 410 to continue monitoring sensed intervals and, whenever a new non-sustained arrhythmia is detected, update the calculated metric of non-sustained arrhythmia.

The metric determined at step 425 preferably reflects changes in the frequency or duration of non-sustained arrhythmias, which could indicate a worsening of factors responsible for triggering a sustained arrhythmia. In one embodiment, the metric calculated at step 425 may be the frequency of non-sustained episodes determined as the number of episodes occurring within a predetermined amount of time. A metric may alternatively be the average duration of a given number of non-sustained episodes or the average of all non-sustained episodes occurring within a predetermined amount of time. Other data that may be stored for use in calculating a non-sustained arrhythmia metric may be an average cycle interval or a characteristic of the EGM signal during non-sustained arrhythmias. In patients that experience non-sustained arrhythmias, EGM or cycle interval information obtained during non-sustained arrhythmias may be more specific for predicting a sustained arrhythmia than EGM or cycle interval data obtained during sinus rhythm.

Figure 4:
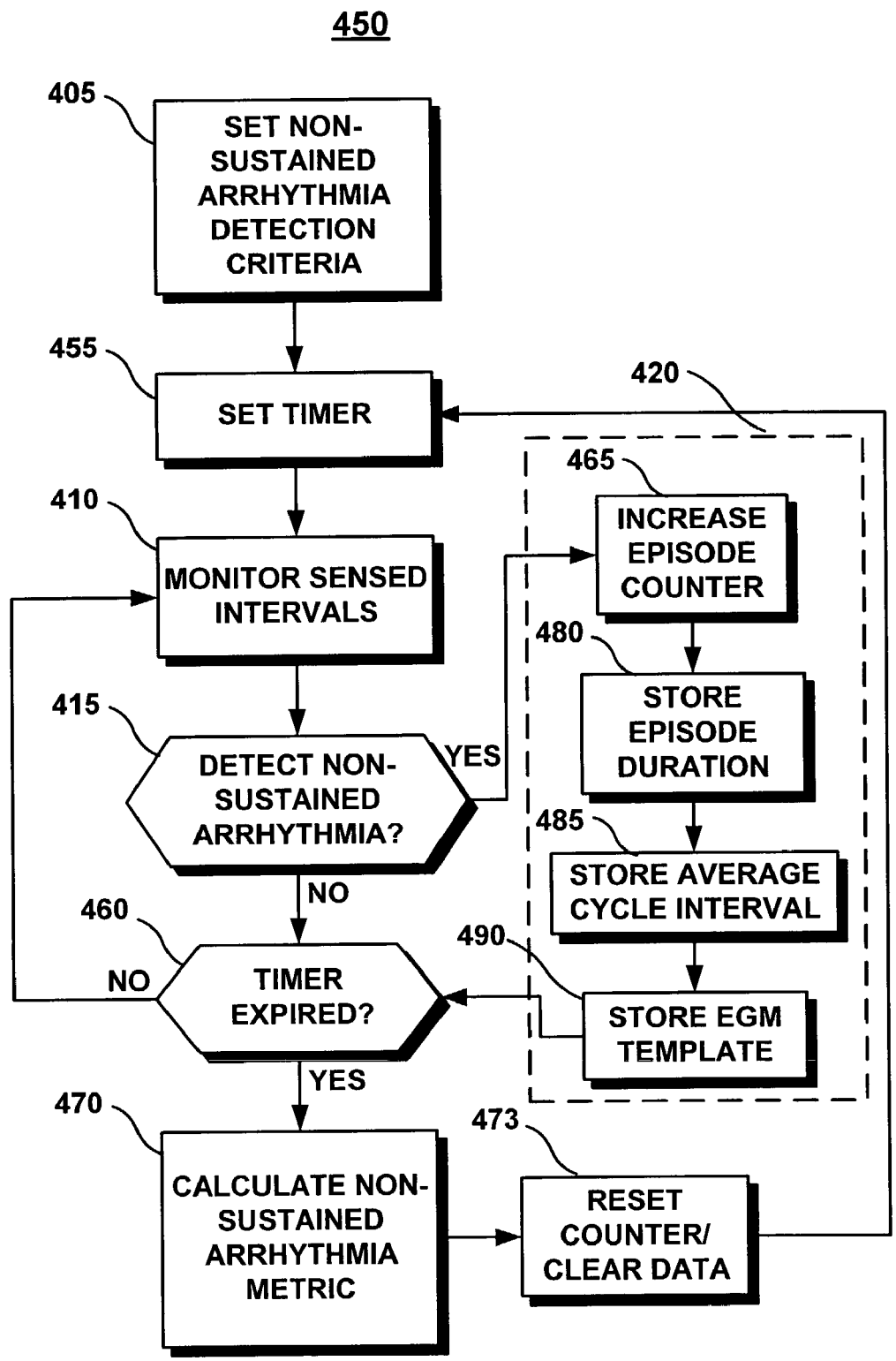
FIG. 4 is a flow chart summarizing specific steps included in one embodiment of the method of FIG. 3 for calculating one or more metrics of non-sustained arrhythmias.

FIG. 4 is a flow chart summarizing specific steps included in one embodiment of the method of FIG. 3 for calculating one or more metrics of non-sustained arrhythmias. Identically numbered steps included in method 450 of FIG. 4 correspond to those in method 400 of FIG. 3. Thus, method 450 begins at step 405 by setting non-sustained arrhythmia detection criteria as described above. At step 455, a timer is set to a predetermined interval of time during which the number of non-sustained arrhythmia episodes will be counted. The timer should be set according to the time resolution desired for measuring episode frequency, for example the number of non-sustained arrhythmia episodes occurring in one hour, 4 hours, 8 hours, 24 hours, etc.

At step 410, sensed intervals are monitored until a non-sustained arrhythmia is detected at decision step 415 or until the timer is expired at decision step 460. If a non-sustained arrhythmia is detected, the data collection and storage step 420 of FIG. 3, indicated by dashed line in FIG. 4, begins. Data collection and storage step 420 may include storing a number of variables relating to the detected episode. In a preferred embodiment the frequency of non-sustained arrhythmias is determined by counting the number of episodes occurring within a specified period of time tracked by the timer set at step 455. Therefore, upon detection of a non-sustained arrhythmia, an episode counter is increased by one at step 465.

Another variable that may be used in determining a metric of non-sustained arrhythmias may be the duration of non-sustained episodes. At step 480, the duration of the detected non-sustained arrhythmia episode may be stored in memory 226. The duration may be stored as the number of intervals meeting the detection criteria. The duration may alternatively be stored in units of time.

The method 450 may further include the ability to determine a metric relating to cardiac cycle intervals or the sensed EGM signal morphology during non-sustained arrhythmias. If the cardiac cycle intervals or features of the EGM signal morphology during non-sustained arrhythmias approach values typical of a sustained arrhythmia, the occurrence of a sustained arrhythmia may be imminent.

Therefore, at step 485 one or more average cycle intervals may be determined from the detected episode and stored in memory 226. The average cycle intervals stored at step 485 may include but are not limited to an average PP interval, RR interval, PR interval, RP interval, RT interval or any other interval occurring within or between consecutive cardiac cycles during a non-sustained arrhythmia. Alternatively or additionally to storing an average cycle interval, a minimum, maximum, or median cycle interval may also be stored.

A template of the EGM signal may be digitized and stored at step 490. The template may be taken from one cardiac cycle during a non-sustained arrhythmia episode or an average of the EGM signal sampled over a given number of cardiac cycles during a non-sustained arrhythmia episode. Characteristic signal features may also be determined and stored, such as, but not limited to, a peak amplitude, a slope, or a frequency component.

After storing the desired episode data, microprocessor 224 determines if the timer has expired at decision step 460. If not, microprocessor 224 returns to step 410 to continue monitoring the sensed cardiac intervals. After the timer expires at step 460, a non-sustained arrhythmia metric is calculated at step 470 based on the data collected for all detected, non-sustained episodes. The metric is stored in memory 226 and is then available for use by other algorithms or for downloading to an external device for physician analysis. The episode counter may then be reset to zero and other stored data may be cleared from memory 226 at step 473. The timer is reset at step 455 and the process, beginning at step 410 for monitoring the sensed intervals, may be repeated allowing the non-sustained arrhythmia metric to be recurrently calculated based on new non-sustained arrhythmia episodes.

One or more metrics may be calculated at step 470. One metric may be equal to the value of the episode counter and represent the frequency of non-sustained arrhythmia episodes during one timer cycle. Another metric may be calculated as the average of the stored episode durations or the total number of non-sustained arrhythmia intervals occurring during a timer interval calculated as the sum of all the stored episode durations. Alternatively, a metric may be the product of the number of episodes detected and the average of all episode durations.

One or more non-sustained arrhythmia metrics may also be determined at step 470 based on the stored cycle interval(s) and/or the EGM morphology template data. A non-sustained arrhythmia metric may be calculated as an average of cycle interval data collected at step 485 or an average of a characteristic feature of the EGM template stored at step 490.

A metric of non-sustained arrhythmias may also be calculated as a function of two or more of the stored variables.

For example, a non-sustained arrhythmia metric (NSAmetric) may be a weighted sum of variables calculated according to Equation 1:

$$NSA\text{metric} = a_1 NSA(\text{count}) + a_2 NSA(\text{duration}) + a_3 (NSA(\text{count}) \times NSA(\text{duration})) + a_4 PP\text{interval} + a_5 RR\text{interval} + a_6 EGM\text{template}$$

wherein, NSA(count) represents the number of non-sustained arrhythmia episodes detected during a specified period of time; NSA(duration) represents the average of the stored episode durations; PPinterval is the average atrial interval and RRinterval is the average ventricular interval determined from the stored cycle interval data for all episodes; and EGMtemplate represents any quantitative value derived from digitized EGM signals occurring during the detected non-sustained episodes. Weighting factors $a_1$ through $a_6$ may be assigned any nominal, real value, including zero, and may be tailored to an individual patient based on the patient's history of non-sustained arrhythmias and sustained arrhythmias.

Figure 5:
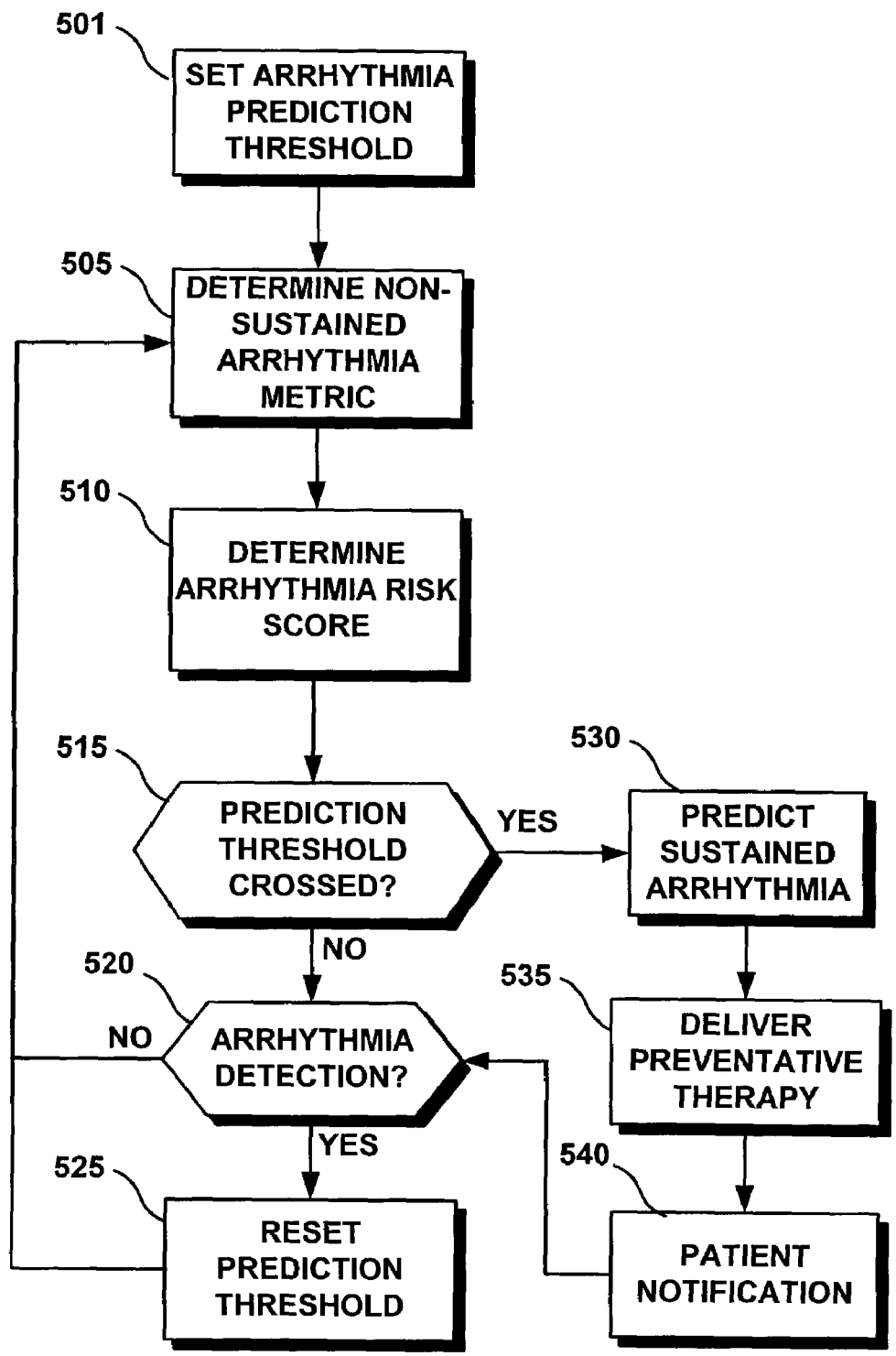
FIG. 5 is a flow chart summarizing a method for predicting a sustained arrhythmia based on a metric of non-sustained arrhythmias.

In the methods shown in FIG. 4, a timer is set to a specified period of time during which data is collected relating to each non-sustained arrhythmia episode detected during that time. A non-sustained arrhythmia metric is recurrently calculated after the specified time period has elapsed. Therefore, a period of data collection precedes the determination of a non-sustained arrhythmia metric. In an alternative embodiment, a metric may be re-determined after each non-sustained arrhythmia detection. An initial period of data collection may be required to calculate the first value of the metric after which the metric may be updated upon each non-sustained arrhythmia detection. This approach would allow the metric to be updated more frequently such that, if there is a sudden change in the occurrence of non-sustained arrhythmias, the metric will reflect this change more quickly allowing the metric to more promptly influence other algorithms in which the metric is used, such as for predicting the occurrence of a sustained arrhythmia. A metric may be updated based on the most recently detected non-sustained arrhythmia or a given number of the most recently detected non-sustained arrhythmias FIG. 5 is a flow chart summarizing a method for predicting a sustained arrhythmia based on a metric of non-sustained arrhythmias. Method 500 begins at step 501 by setting an initial, nominal arrhythmia prediction threshold. The nominal prediction threshold is preferably a programmable setting that defines a limit for an arrhythmia risk score, which, if crossed, indicates that a sustained arrhythmia is highly likely to occur. A patient's history of arrhythmias may be considered when selecting the nominal prediction threshold.

At step 505, a metric of non-sustained arrhythmias is determined according to the methods described above in conjunction with FIG. 4 based on the frequency and/or duration of non-sustained arrhythmia episodes and/or other optional factors such as non-sustained arrhythmia cycle intervals or EGM signal characteristics. At step 510, an arrhythmia risk score is determined. An arrhythmia risk score may be equal to a non-sustained arrhythmia metric. For example, the arrhythmia risk score may equal a non-sustained arrhythmia metric determined as the number of episodes or the average duration of non-sustained arrhythmias occurring in a specified period of time. The arrhythmia risk score may alternatively equal a non-sustained arrhythmia metric calculated as the product of the number of episodes and the average duration of non-sustained arrhythmias occurring in a specified period of time.

The arrhythmia risk score may alternatively be a function of one or more non-sustained arrhythmia metrics and other factors that may be predictive of an arrhythmia, such as the frequency of premature contractions, heart rate variability or other factors. The arrhythmia risk score, for example, may be a weighted sum of a non-sustained arrhythmia metric and the number of premature contractions within a given period of time, calculated according Equation 3:

$$\text{Risk score} = b_1 NSA\text{metric} + b_2 PC(\text{count}) \quad (3)$$

wherein NSAmetric may be any non-sustained arrhythmia metric such as the metric calculated according to Equation 1 above; and PC(count) represents the number of premature contractions occurring during a specified period of time. The weighting factors $b_1$ and $b_2$ may be assigned any real, nominal values, including zero or one. The weighting factors may be tailored to an individual patient based on the patient's history of non-sustained arrhythmias, premature contractions, and sustained arrhythmias.

If a sustained arrhythmia has been detected previously, variables relating to the sustained arrhythmia may be compared to variables relating to non-sustained arrhythmias. Cycle intervals during a detected sustained arrhythmia may be collected, averaged if desired, and stored. A template of the EGM during a sustained arrhythmia may be digitized and stored to allow the template to be compared to a template acquired during a non-sustained arrhythmia. Alternatively, EGM signal characteristics may be derived from a sustained arrhythmia EGM template. A difference, ratio or other mathematical relationship between sustained and non-sustained arrhythmia cycle intervals or EGM signal template characteristics could be included in a calculation of a risk score. For example, an arrhythmia risk score may be calculated as:

$$\text{Risk Score} = c_1 NSA(\text{count}) + c_2 NSA(\text{duration}) + c_3 (NSA(\text{count}) \times NSA(\text{duration})) + c_4 \Delta PP\text{interval} + c_5 \Delta RR\text{interval} + c_6 \Delta EGM\text{template} \quad (3)$$

wherein $\Delta PP$interval is the difference between the average PP interval determined during a previously detected sustained arrhythmia and the PP interval determined for non-sustained arrhythmias; $\Delta RR$interval is the difference between the average RR intervals during sustained and non-sustained arrhythmias, and $\Delta EGM$template is the difference between a characteristic value of the EGM signal template acquired during sustained and non-sustained arrhythmias.

At decision step 515, microprocessor 224 determines if the risk score calculated at step 510 crosses the prediction threshold. If the prediction threshold is crossed, microprocessor 224 issues a signal predicting that a sustained arrhythmia is likely to occur at step 530. This prediction signal may trigger the delivery of an arrhythmia prevention therapy at step 535. Preventative therapies may include pacing therapies, drug delivery, or neurostimulation. For example, overdrive pacing therapies delivered by ICD 10 may prevent the onset of a predicted arrhythmia. In alternative embodiments, the ICD 10 may be in telemetric communication with another implanted or external medical device such as a drug pump or neurostimulator. The microprocessor 224 may generate a telemetric signal to trigger the administration of a drug or the initiation of neurostimulation that may be in the form of vagal stimulation or spinal cord stimulation in an attempt to counteract the factors that may be triggering an arrhythmia. Alternatively, the method 500 may be implemented directly in a drug delivery device, a neurostimulator, or another medical device capable of delivering a preventative therapy at step 535.

At step 540, an optional patient notification signal may be generated by notification system 150 to alert the patient to the predicted arrhythmia. By notifying the patient, the patient is able to alter their current activity, seek medical attention, or self-administer a prescribed therapy. The method 500 may then be terminated or continue to decision step 520 to determine if an arrhythmia occurs. A sustained arrhythmia may still occur if the preventative therapy was not effective or delivered too late.

If an unpredicted or unpreventable arrhythmia occurs at step 520, anti-arrhythmia therapy may be delivered according to normal device operations. The initial, nominal arrhythmia prediction threshold may then be reset at step 525 based on the value of the non-sustained arrhythmia metric at the time of the arrhythmia occurrence. The prediction threshold may be set, for example, as a percentage of the value of the non-sustained arrhythmia metric at the time of sustained arrhythmia detection. The prediction threshold is preferably some value less than the value of the metric at the time of sustained arrhythmia detection otherwise a prediction of a future arrhythmia may occur too late. By basing the arrhythmia predication threshold on the value of one or more non-sustained arrhythmia metrics at the time of a sustained arrhythmia occurrence within an individual patient, the predictive success of method 500 for that patient may be improved. The method 500 may then return to step 505 to continue detecting non-sustained arrhythmias and re-determining a non-sustained arrhythmia metric.

Before a sustained arrhythmia becomes imminent, the incidence of non-sustained arrhythmias may increase, in frequency and/or in duration. The number of anti-arrhythmia therapies delivered by a conventional ICD may therefore increase due to increased arrhythmia detections based on static arrhythmia detection parameters. Even when a sustained arrhythmia is not imminent, a patient that experiences recurrent non-sustained arrhythmias may be subject to repeated therapy delivery. Adjusting the arrhythmia detection parameters according to a metric of non-sustained arrhythmias may avoid delivering unneeded therapies during episodes that would otherwise spontaneously terminate. Therapies can be painful to the patient, use large amounts of battery charge, and can accelerate or otherwise worsen the severity of the arrhythmia in some cases. Adjustable detection parameters may conserve therapy delivery for when it is truly needed to treat a sustained arrhythmia.

Figure 6:
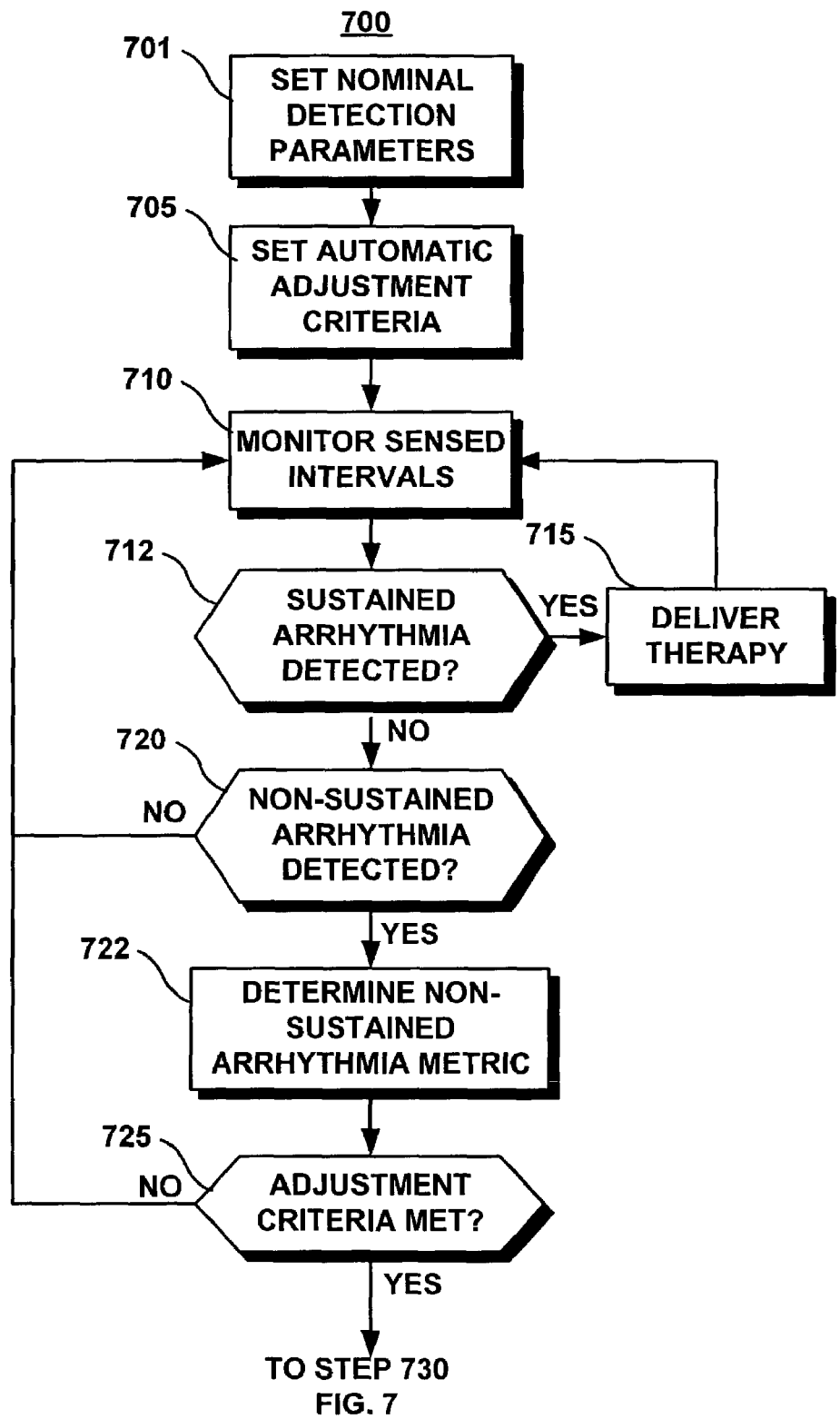
FIGS. 6 and 7 are a flow chart summarizing the steps included in a method for automatically adjusting arrhythmia detection parameters based on a metric of non-sustained arrhythmias.
Figure 7:
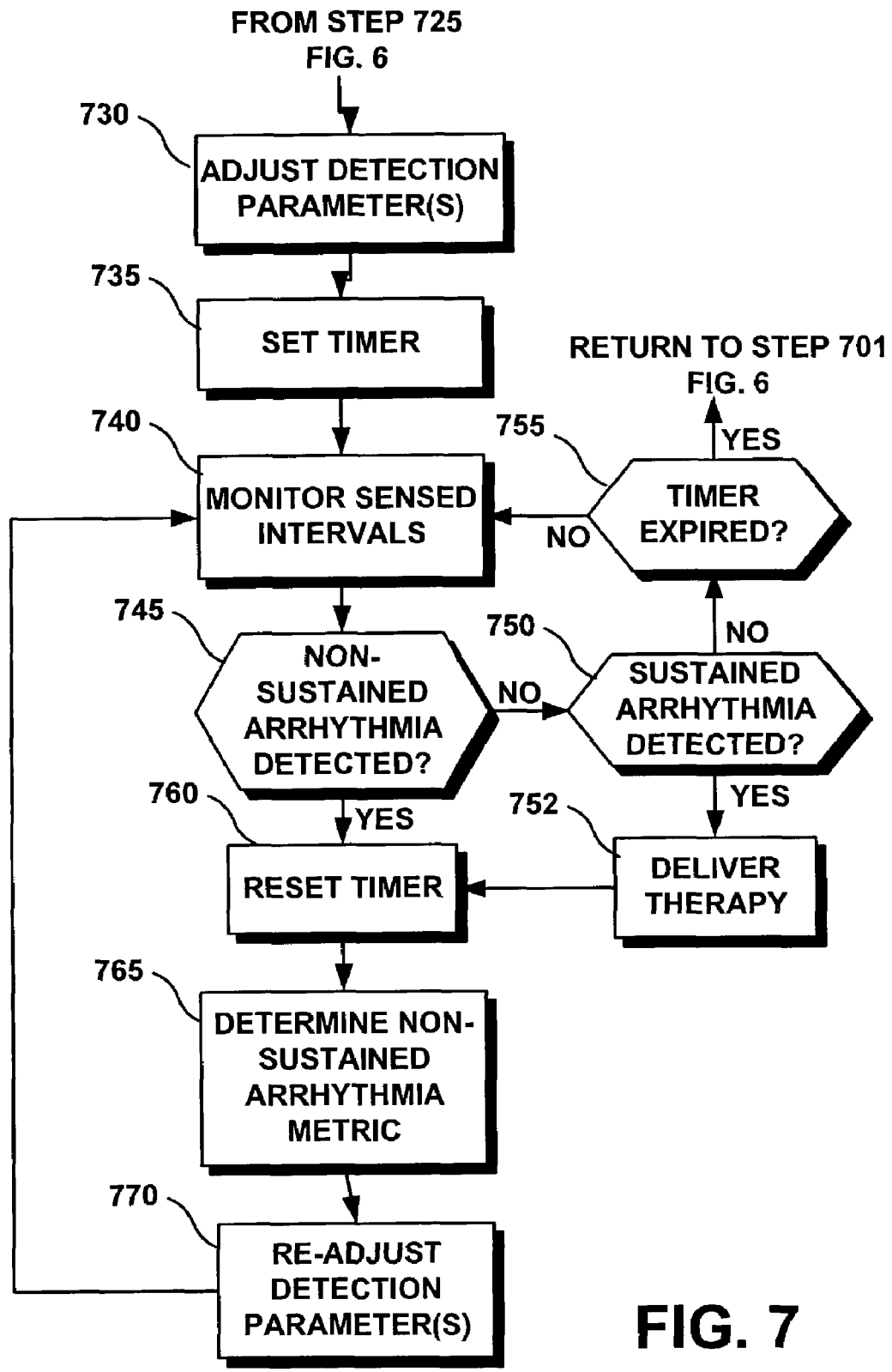

FIGS. 6 and 7 are a flow chart summarizing the steps included in a method for automatically adjusting arrhythmia detection parameters based on a metric of non-sustained arrhythmias. The method 700 shown in FIGS. 6 and 7 may be included in an implantable medical device in addition to the arrhythmia prediction method 500 of FIG. 5. Alternatively, method 700 may operate exclusively of method 500. At step 701, nominal non-sustained arrhythmia and sustained arrhythmia detection parameters are set. These detection parameters are typically programmable parameters including a detection interval and a number of intervals to detect (NID).

At step 705, criteria are set for triggering an automatic adjustment of the nominal sustained arrhythmia detection parameters. These criteria may be based on one or more metrics of non-sustained arrhythmias, which may be related to the frequency or duration of non-sustained arrhythmia episodes, the cycle interval stability during non-sustained episodes or other EGM characteristics. Other automatic adjustment criteria may include simply the detection of a non-sustained arrhythmia, examination of trends of recently calculated non-sustained arrhythmia metrics, or other indicators of heart function. When the automatic adjustment criteria are met, the nominally programmed sustained arrhythmia detection parameters are adjusted, as will be described below.

If method 700 is executed concurrently with method 500 of FIG. 5, automatic adjustment criteria may optionally include a criterion that no prediction of a sustained arrhythmia has been made. If a sustained arrhythmia is predicted to be imminent, maintaining more stringent detection parameters may be preferred in some cases. However, dynamic detection of non-sustained arrhythmias, according to automatically adjusted detection parameters, may be desired in patients experiencing frequent non-sustained episodes whether a sustained arrhythmia is predicted or not.

At step 710 sensed intervals are monitored to determine if an arrhythmia is detected. If a sustained arrhythmia is detected at decision step 712, an appropriate anti-arrhythmia therapy is delivered at step 715 according to normal device operations. If a non-sustained arrhythmia is detected at decision step 720, a metric of non-sustained arrhythmias is determined at step 722. The metric may be determined according to the methods described above in conjunction with FIG. 4 and based on the frequency of episode detection, the episode duration, the episode cycle intervals, EGM or other characteristics of the non-sustained arrhythmia.

At decision step 725, microprocessor 224 determines if the automatic adjustment criteria are met. This determination may involve comparing the metric determined at step 722 to a predetermined threshold or range of values or determining if other criteria, as described above, have been met. If automatic adjustment criteria are met, the method 700 will proceed to step 730 of FIG. 7. If the criteria are not met, method 700 returns to step 710 to continue monitoring sensed intervals until the automatic adjustment criteria are met.

At step 730, the sustained arrhythmia detection parameters are automatically adjusted. At step 735, an optional timer is set to limit the period of time in which the adjusted detection parameters are in effect. Underlying factors that trigger the occurrence of arrhythmias may change such that the patient no longer experiences non-sustained arrhythmias but is still at risk for a sudden sustained arrhythmia. The sustained arrhythmia detection parameters, therefore, preferably revert back to nominal programmed values after a period of no detected non-sustained episodes.

With the adjusted sustained arrhythmia detection parameters in effect, sensed cardiac intervals are monitored at step 740 for either a sustained or non-sustained arrhythmia. If another non-sustained arrhythmia is detected at decision step 745, the timer is reset at step 760. The non-sustained arrhythmia metric may be re-determined at step 765 following the new non-sustained episode detection and, if necessary, the sustained arrhythmia detection parameters may be re-adjusted at step 770. The method 700 then returns to step 740 to continue monitoring for sustained or non-sustained arrhythmias.

If no non-sustained arrhythmia episodes are detected at decision step 745, but a sustained arrhythmia is detected any time during the operations of method 700, as determined at decision step 750 based on the adjusted detection parameter, the appropriate anti-arrhythmia therapy is delivered at step 752 according to normal device operations. The timer is then reset at step 760 and the method 700 will return to step 740 to continue to monitor sensed intervals for arrhythmias (no changes will be made at this time to the non-sustained arrhythmia metric or detection parameter at steps 765 and 770 because the detected arrhythmia was a sustained arrhythmia). When method 700 is operating concurrently with method 500 for arrhythmia prediction, the detection of an arrhythmia at step 750 would also cause an adjustment of the arrhythmia prediction threshold (shown at step 525 in FIG. 5).

If no sustained arrhythmias are detected at decision step 750, and the timer has not expired as determined at decision step 755, the microprocessor 224 continues to monitor the sensed cardiac intervals at step 740 for non-sustained or sustained arrhythmia episodes. If the timer has expired at decision step 755, method 700 returns to step 701 of FIG. 6 to reset the detection parameters to the nominal programmed values and the method 700 may begin again.

Figure 8:
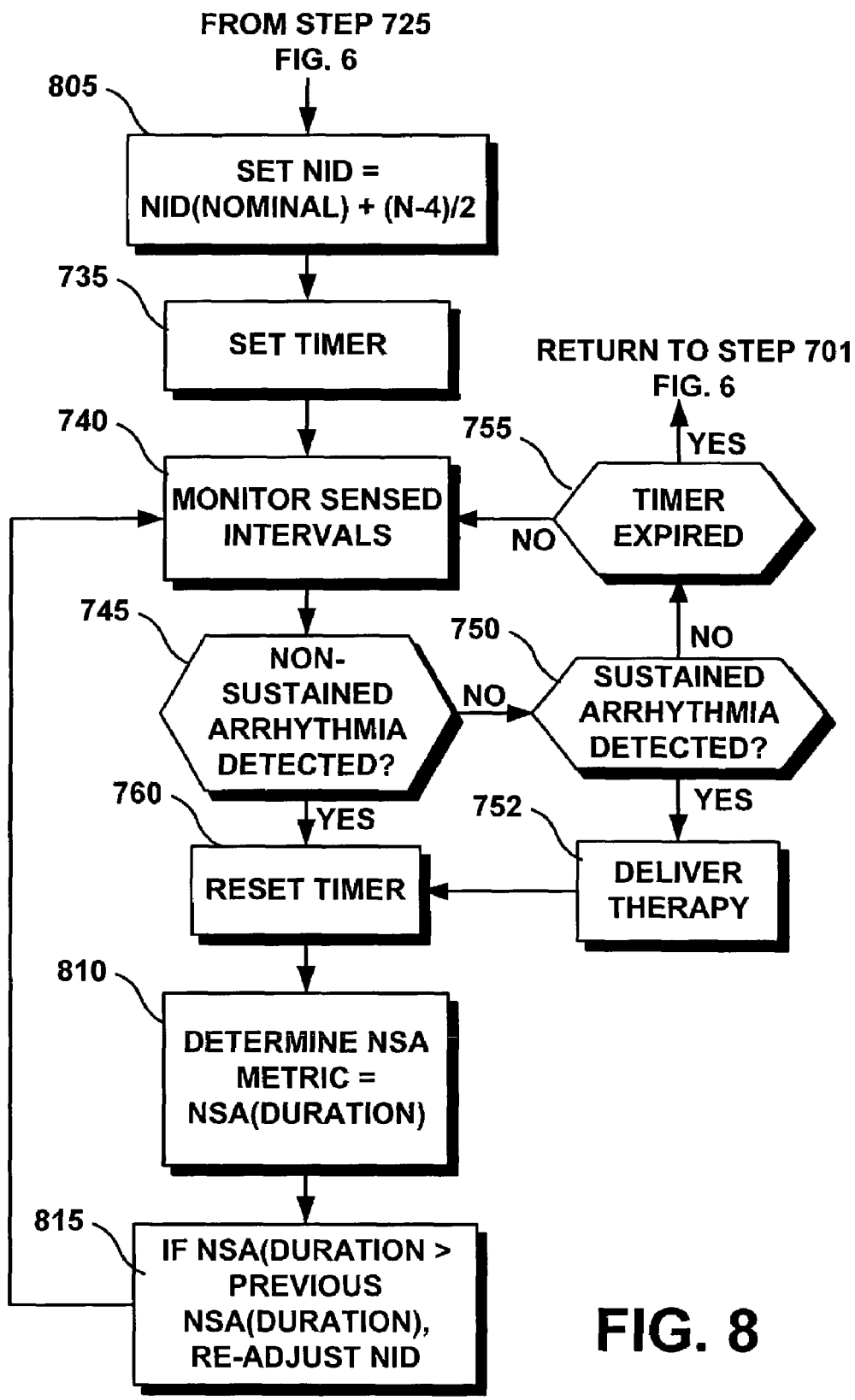
FIG. 8 is a flow chart detailing specific steps included in one embodiment of the method of FIGS. 6 and 7 wherein the required number of intervals to detect a sustained arrhythmia is automatically adjusted based on the duration of a detected non-sustained arrhythmia.

FIG. 8 is a flow chart detailing specific steps included in one embodiment of the method of FIGS. 6 and 7 wherein the required number of intervals to detect a sustained arrhythmia is automatically adjusted based on the duration of a detected non-sustained arrhythmia. Identically labeled steps included in the method of FIG. 8 correspond to those shown in FIG. 7, and steps shown in FIG. 8 represent a continuation from step 725 of FIG. 6. After determining that automatic parameter adjustment criteria are met at step 725 in FIG. 6, the method 700 may continue to step 805 of FIG. 8 where the number of intervals to detect (NID) is automatically adjusted. In the embodiment of FIG. 8, automatic parameter adjustment criteria simply require that a non-sustained arrhythmia has been detected. Automatic adjustment of NID may then be made based on the duration of the detected non-sustained episode.

In one embodiment, NID may be adjusted according to the following equation:

$$NID = NID(nominal) + (NSA(duration) - 4)/2 \quad (4)$$

wherein NID(nominal) is the nominally programmed number of intervals to detect and NSA(duration) is the duration of the most recently detected non-sustained arrhythmia expressed as the number of intervals occurring during the non-sustained episode. NSA(duration) may alternatively be the average duration of a specified number of previously detected non-sustained arrhythmias or the average duration of all non-sustained episodes detected during a specified time period.

NID may alternatively be increased by a fixed preset increment, a percentage of the nominal NID, a percentage of NSA(duration) or other increments based on a nominal NID value or the non-sustained arrhythmia metric.

Steps 735 through 760 are performed as described previously in conjunction with FIG. 7. At step 810, the non-sustained arrhythmia metric is re-determined following the detection of a new non-sustained arrhythmia episode. In this embodiment, the metric is the duration, measured as the number of intervals, of the detected non-sustained arrhythmia episode. At step 815, the arrhythmia detection parameter, NID, may be readjusted, if necessary, based on the updated non-sustained arrhythmia metric, NSA(duration). If the non-sustained arrhythmia duration determined at step 810 is greater than the previously determined duration, then the detection parameter NID may be increased again, according to Equation (4) above, using the new NSA(duration) value. If the NSA(duration) determined at step 810 is less than the previously determined duration, then no adjustment to the detection parameter NID is necessary.

The adjusted NID is preferably limited to some maximum value. Even if the detected arrhythmia may spontaneously terminate at some point without anti-arrhythmia therapy, a prolonged arrhythmia may cause hemodynamic compromise or other symptoms. Treatment of a prolonged arrhythmia, whether it ultimately would be sustained or not, may be preferred over allowing the arrhythmia to persist until the patient becomes symptomatic. Adjustment of NID according to Equation 4 automatically limits the maximum adjusted NID setting. An illustrative example of this self-limiting process is provided in FIG. 9.

Figure 9:
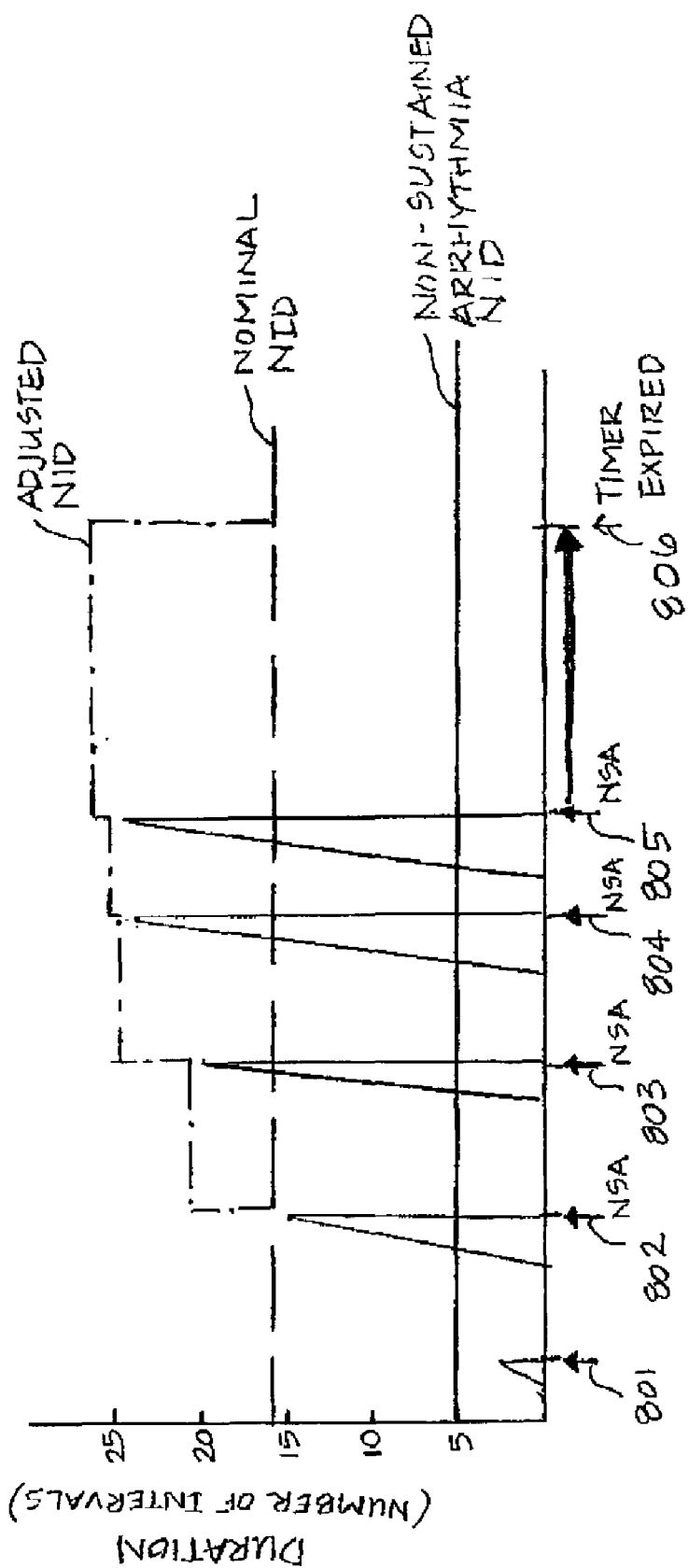
FIG. 9 is a timeline depicting an example of the operation of the method of FIG. 8.

FIG. 9 is a timeline depicting an example of the operation of the method of FIG. 8. The nominal NID for sustained arrhythmias is initially programmed to 16 intervals in this example. The number of intervals to detect non-sustained arrhythmias is fixed at 5 intervals. A run of four sensed intervals occurs at a time indicated by arrow 801 that meet the interval detection criteria but do not meet the NID for non-sustained arrhythmia detection. A non-sustained arrhythmia of 15 intervals in duration is detected at a time indicated by arrow 802. Based on this non-sustained arrhythmia detection, the number of intervals to detect (NID) a sustained arrhythmia is adjusted to 21, or the nearest available setting, according to Equation (4) above and calculated, using integer math to truncate the value to a whole number, as:

$$NID = 16 + (15-4)/2 = 16+5 = 21.$$

Another non-sustained arrhythmia detection having a duration of 20 intervals occurs at a time indicated by arrow 803. The sustained NID is re-adjusted to 24:

$$NID = 16 + (20-4)/2 = 16+8 = 24.$$

A fourth non-sustained arrhythmia is detected at a time indicated by arrow 804 having a duration of 23 intervals. The sustained NID is re-adjusted to 25:

$$NID = 16 + (23-4)/2 = 16+9 = 25.$$

Another non-sustained episode is detected having a duration of 24 intervals, indicated by arrow 805, causing the NID will be increased to 26:

$$NID = 16 + (24-4)/2 = 16+10 = 26.$$

If yet another non-sustained episode where to be detected having a the maximum possible duration of 25 intervals under the current detection parameters, the sustained arrhythmia NID will remain at 26:

$$NID = 16 + (25-4)/2 = 16+10 = 26.$$

Thus, using the Equation 4 to adjust NID based on the metric of non-sustained episode duration automatically limits the maximum value that the adjusted NID will reach.

In FIG. 9, no additional non-sustained arrhythmia detections are made for a specified time interval occurring between arrows 805 and 806. At the end of this time interval, as determined by the expiration of a timer at step 755 of FIG. 8, the automatic adjustment method restarts at step 701 of FIG. 6 wherein the sustained NID is reset to the nominal value of 16 in this example.

The automatic adjustment of NID in this hypothetical example prevented the delivery of anti-arrhythmia therapy from treating the non-sustained arrhythmias occurring at arrow 803, arrow 804 and arrow 805, which would have otherwise been detected as sustained arrhythmias according to the nominal NID detection criteria. Thus, automatic adjustment of arrhythmia detection parameters may prevent unneeded anti-arrhythmia therapies when the incidence of non-sustained arrhythmias may be increasing.

A method and apparatus have been described for determining a metric of non-sustained arrhythmias. Methods have also been described for predicting a sustained arrhythmia based on a metric of non-sustained arrhythmia. These methods are expected to enable preventative arrhythmia therapies to be delivered in a timely and effective manner and thereby reduce the risk of life-threatening arrhythmias overall. Furthermore, methods have been described for automatically adjusting sustained arrhythmia detection parameters based on a metric of non-sustained arrhythmias, which could reduce the likelihood of delivering unneeded anti-arrhythmia therapies. The methods included in the present invention may be applied to various types of arrhythmias including atrial or ventricular tachycardia or fibrillation. Aspects included in the present invention described in conjunction with an ICD could also be implemented in external cardioverter defibrillators, external or internal cardiac rhythm monitoring devices, or external or internal rhythm management devices, which may include drug pumps or neurostimulators. As such, the above disclosure should be considered exemplary, rather than limiting, with regard to the following claims.

What is claimed is:

1. A method for determining a metric of the occurrence of non-sustained arrhythmias comprising;
    detecting non-sustained arrhythmia episodes as episodes;
    storing characteristic data related to the non-sustained arrhythmia; and
    calculating a metric of non-sustained arrhythmias based on the stored data; and
    adjusting a parameter for detecting a sustained arrhythmia based on the metric of non-sustained arrhythmia occurrence, wherein stored characteristic data includes one of a number of non-sustained arrhythmia episodes within a specified period of time, a duration of a non-sustained arrhythmia episode, a cycle length during a non-sustained arrhythmia episode, and a cardiac signal morphology during a non-sustained arrhythmia episode.

2. The method according to claim 1, further including a method for predicting the occurrence of a sustained arrhythmia based on the metric of non-sustained arrhythmias comprising:
    calculating an arrhythmia risk score based on a metric of non-sustained arrhythmias;
    comparing the risk score to a predefined or automatically updated threshold criteria; and
    predicting that a sustained arrhythmia is likely to occur with a high probability if the risk score meets or exceeds the threshold criteria.

3. The method according to claim 2, further including delivering a preventative therapy if a sustained arrhythmia is predicted to occur.

4. The method according to claim 2, further including adjusting the threshold criteria based on a detected sustained arrhythmia.

5. The method according to claim 1, wherein the parameter for detecting a sustained arrhythmia is adjusted by increasing the number of cardiac cycle intervals occurring in an arrhythmia detection zone required to detect a sustained arrhythmia.

6. The method according to claim 5, wherein the parameter is adjusted by varying the duration of non-sustained arrhythmia episodes.

* * * * *